(12) United States Patent
De Gooyer et al.

(10) Patent No.: US 9,193,485 B2
(45) Date of Patent: Nov. 24, 2015

(54) FOLDING DEVICE AND ASSEMBLY FOR MAKING A FOLD IN A FOLDABLE WRAPPING MATERIAL OR MATERIAL TO BE WRAPPED

(75) Inventors: Gert De Gooyer, MG Veenendaal (NL); Aalf Wijnia, BJ Barneveld (NL); Peter Drost, PR Veenendaal (NL); Ton De Boer, TS Baarn (NL)

(73) Assignee: VMI HOLLAND B.V., Epe (NL)

( * ) Notice: Subject to any disclaimer, the term of this patent is extended or adjusted under 35 U.S.C. 154(b) by 1003 days.

(21) Appl. No.: 13/256,961

(22) PCT Filed: Mar. 19, 2010

(86) PCT No.: PCT/NL2010/050145
§ 371 (c)(1),
(2), (4) Date: Oct. 13, 2011

(87) PCT Pub. No.: WO2010/110657
PCT Pub. Date: Sep. 30, 2010

(65) Prior Publication Data
US 2012/0021885 A1    Jan. 26, 2012

(30) Foreign Application Priority Data

Mar. 26, 2009  (NL) ..................................... 2002676

(51) Int. Cl.
| | |
|---|---|
| *B65B 11/02* | (2006.01) |
| *B31F 1/00* | (2006.01) |
| *B65B 11/48* | (2006.01) |
| *B65H 45/12* | (2006.01) |
| *B31B 3/52* | (2006.01) |
| *A61B 19/08* | (2006.01) |

(52) U.S. Cl.
CPC ............... *B65B 11/02* (2013.01); *B31F 1/0006* (2013.01); *B65B 11/48* (2013.01); *B65H 45/12* (2013.01); *A61B 19/08* (2013.01); *B31B 3/52* (2013.01)

(58) Field of Classification Search
USPC ............. 53/399, 410, 416, 128.1, 138.1, 140, 53/203, 209
IPC ............ B65B 11/00,11/004, 11/48; B31B 3/26, B31B 3/52
See application file for complete search history.

(56) References Cited

U.S. PATENT DOCUMENTS

| | | | | |
|---|---|---|---|---|
| 4,660,351 | A * | 4/1987 | Saitoh | 53/417 |
| 4,820,255 | A * | 4/1989 | Nanami | 493/451 |
| 4,834,700 | A * | 5/1989 | Kondo et al. | 493/463 |
| 5,375,393 | A * | 12/1994 | Baker et al. | 53/429 |
| 5,456,651 | A * | 10/1995 | Baker et al. | 493/405 |
| 7,076,932 | B2 * | 7/2006 | Rubin | 53/461 |

* cited by examiner

*Primary Examiner* — Christopher Harmon
(74) *Attorney, Agent, or Firm* — Ladas & Parry LLP (57) ABSTRACT

Folding device for making a fold in a first direction in a foldable material, wherein the folding device comprises a clamping unit and a folding unit, the clamping unit comprising first and second clamping fingers, which with respect to each other can be moved apart and towards each other for clamping the material in between them, the folding unit being placed next to the clamping unit in a direction transverse to the first direction, and comprising a first and a second folding arm, which with respect to each other can be moved apart and towards each other, the first folding arm comprising two first folding fingers that extend in a direction of the first folding arm and are spaced apart from each other transverse to the first direction, the second folding arm comprising at least one second folding finger that extends in the direction of the first folding arm, the second folding finger being movable to between the first folding fingers.

16 Claims, 10 Drawing Sheets

FOLDING DEVICE AND ASSEMBLY FOR MAKING A FOLD IN A FOLDABLE WRAPPING MATERIAL OR MATERIAL TO BE WRAPPED

BACKGROUND OF THE INVENTION

The invention relates to a folding device for making a fold in a first direction in a foldable wrapping material or material to be wrapped. The invention further relates to a folding assembly for wrapping one or more products to be wrapped in a wrapping material, which assembly comprises a folding device. The invention further relates to a method for making a fold in a first direction in a foldable wrapping material or material to be wrapped.

In the medical field, for instance in the field of eye surgery, medical instruments and the like have up until now been manually wrapped in a sterile manner in wrapping material, particularly surgical sheets, into a closed package. Irrespective of the dimensions of the medical instruments to be wrapped said surgical sheets have the same size, so that when the closed package is unwrapped the surgical sheet fully covers an instrument table. The surgical sheet therefore has dimensions that generally are much larger than necessary for wrapping the medical instruments, so that the surgical sheet is folded once or several times in order to correctly wrap the products to be wrapped. Folding the wrapping material and wrapping the products to be wrapped is adapted to among others the required medical instruments or depending on the wishes of the surgeon, which results in the dimensions of the products to be wrapped to vary and consequently the way of wrapping and folding also varies. Although manually wrapping is reasonably satisfactory, in daily practice an undesirable large number of packages turn out not to have been wrapped sufficiently sterilely. Moreover manually wrapping proves to take a lot of time, to result in too many pleats in the folding area, and/or not always to be of a reproducible quality.

SUMMARY OF THE INVENTION

It is among others an object of the present invention to provide a folding device with which a foldable material, and particularly a supple material, can be provided with one or more folds by machine.

It is a further object of the present invention to provide an assembly for wrapping one or more products to be wrapped in a substantially rectangular wrapping material, which assembly is able to wrap products in a relatively fast and reproducible manner.

For achieving one or more of the objects mentioned above, the present invention, according to a first aspect, provides a folding device for making a fold in a first direction in a foldable wrapping material or material to be wrapped, wherein the folding device comprises a clamping unit and a folding unit, the clamping unit comprising first and second clamping fingers, which with respect to each other can be moved apart and towards each other for clamping the wrapping material or material to be wrapped in between them, the folding unit being placed next to the clamping unit in a direction substantially transverse to the first direction, and comprising a first and a second folding arm, which with respect to each other can be moved apart and towards each other, the first folding arm comprising two first folding fingers that extend in a direction of the first folding arm and are spaced apart from each other substantially transverse to the first direction, the second folding arm comprising at least one second folding finger that extends in the direction of the first folding arm, the second folding finger of the second arm being movable to between the first folding fingers of the first arm.

Using such a folding device with arms that are able to move apart and towards each other, and which are provided with interlocking folding fingers, makes it possible to provide a foldable material, such as for instance a surgical sheet, with one or more folds in a reproducible manner by machine. In that way particularly in case of wrapping medical instruments it can be ensured that in at least almost all cases the medical instruments are wrapped sterilely.

A further advantage of the device according to the invention is that the degree of overlap of the folded material can also be adjusted by adjusting the distance over which the second folding finger extends between the first folding fingers. In that way the folding of the foldable material, such as for instance the surgical sheet, can be adapted to the desired dimensions of the folded material, and particularly when wrapping medical instruments it can be ensured that the wrapping material in at least almost all cases is fittingly folded for wrapping medical instruments of a certain size.

It has also turned out that the invention can also be used for wrapping other products than medical instruments, and it is not necessary that wrapping takes place in a sterile manner. Moreover it has turned out that other material besides surgical sheets can also be used as wrapping material, and that the folding device can also be used for folding products to be wrapped, particularly textile products.

In an embodiment the first clamping finger of the clamping unit is fixedly connected to the first or second folding arm. In an embodiment the first clamping finger is placed in a direction substantially transverse to the first direction spaced apart next to the folding fingers or folding finger on the folding arm. By combining the clamping and folding unit a compact unit is created, wherein the clamping position is fixed with respect to the folding fingers.

In an embodiment the folding fingers each comprise a free outer end and at the free outer ends of each folding finger at least one rotatable folding roller is provided, a rotary shaft of the folding roller being oriented substantially parallel to the first direction. In that way when the folding fingers interlock, the wrapping material can move between the folding rollers in order to facilitate folding and/or at least partially prevent the causing of rents in the wrapping material.

In an embodiment the clamping fingers each comprise a free outer end and at the free outer end of at least one of the clamping fingers at least one rotatable clamping roller is provided, a rotary shaft of the clamping roller being oriented substantially transverse to the first direction. In that way when clamping the wrapping material can move between the rollers in the first direction, yet a clamping for folding is ensured.

In an embodiment one or more of the folding fingers is planar. In an embodiment an edge at the free outer ends of the folding finger is oriented substantially parallel to the first direction. In that way it is possible that during making a fold the wrapping material is engaged over a sufficiently large surface in order to obtain a reproducible and accurate fold.

In yet a further embodiment of a device according to the invention each clamping finger is planar. In an embodiment an edge at the free outer ends of the clamping finger is oriented substantially parallel to the first direction. In that way it is possible that during clamping the wrapping material is engaged over a sufficiently large surface in order to clamp the wrapping material firmly, reproducibly and accurately.

In an embodiment the first folding arm comprises three folding fingers that are spaced apart from each other, and the second folding arm comprises two folding fingers that are spaced apart from each other, the folding fingers of the second arm being movable to between the outer folding fingers and on both sides of the middle folding finger of the first arm. In that way a surplus of wrapping material in a zigzag shape having a number of folds running substantially parallel to the first direction.

According to a second aspect the invention provides a folding assembly for wrapping one or more products to be wrapped in a wrapping material, which assembly is provided with:
- a table,
- a wrapping material placement means for placing the wrapping material on the table, wherein the wrapping material comprises a first longitudinal side and a second longitudinal side situated opposite thereto,
- a product placement means for placing the one or more products to be wrapped on the wrapping material placed on the table,
- a folding device as described above, for making a fold in a first direction in the wrapping material, wherein the first direction is substantially parallel to the first longitudinal side.

In an embodiment the folding device is a first folding device and the folding assembly furthermore comprises a second folding device, wherein the first folding device can engage the wrapping material at least near an outer end of its first longitudinal side and the second folding device can engage the wrapping material at least near the other outer end of the first longitudinal side. In particular for folding a supple wrapping material it has turned out that when using a folding device at or near both outer ends of the longitudinal side, the part of the wrapping material that is situated between the folding devices is also folded along. In that way it will not be required that the folding device extends over substantially the full length of the longitudinal side.

In an embodiment the first and second folding device are movable into a position on both sides of the first longitudinal side of the wrapping material placed on the table. In an embodiment the first and second folding device can be moved apart and towards each other. In that way it is possible to tauten the material to be folded which improves the reproducibility and the accuracy of making longitudinal folds in the wrapping material.

In an embodiment the folding device or the first and second folding devices can be moved up to a distance above the table. In that way it is possible to arrange an angle of substantially 90° in the wrapping material which is advantageous to the further treatment of the wrapping material.

In an embodiment the folding device or the first and second folding devices are movable from a position near the first longitudinal side of the wrapping material placed on the table into a position near the second longitudinal side of the wrapping material placed on the table. In that way only one longitudinal folding device is required for making longitudinal folds in both longitudinal sides situated opposite each other of the wrapping material. Moreover it is possible in that way that a longitudinal side of the wrapping material can be moved to over and optionally past the products to be wrapped.

In an embodiment the folding assembly is furthermore provided with a transverse folding device for making a transverse fold in the wrapping material, which fold runs transverse to the longitudinal sides, wherein the transverse folding device is provided with at least one folding pin that can be moved to a position extending transverse to the longitudinal sides of the wrapping material and with a folding mechanism for folding the wrapping material over the folding pin. In an embodiment the folding pin is provided with an inclined front side, as a result of which it is possible to facilitate folding to the inside. In that way making a transverse fold in the wrapping material is possible in a fast and reproducible manner.

In an embodiment the folding pin is moveable in a direction transverse to the table. In that way it is possible that the folding pin presses the wrapping material in the direction towards the table so that an accurate transverse fold can be realised.

In an embodiment the folding assembly is furthermore provided with a retaining strip, that can be moved to above a product placed on the wrapping material, which retaining strip can also be moved in a direction transverse to the table. The retaining strip makes it possible that wrapping material folded over the products to be wrapped is kept temporarily in its place by the retaining strip, by pressing the wrapping material on the products to be wrapped.

In an embodiment the folding assembly is furthermore provided with a control device for controlling the operation of the folding device or the first and second folding device, the transverse folding device and the retaining strip. In an embodiment the folding assembly is furthermore provided with input means for entering data regarding the dimensions of the products to be wrapped to the control device. In an alternative embodiment the folding assembly is furthermore provided with a measurement device for measuring the dimensions of the products to be wrapped and for providing the control device with a signal indicative of the measured dimensions. By using such a control device and a measurement device it is possible to let the reproducible and accurate wrapping of products take place largely automatically.

In an embodiment, based on the dimensions of the products to be wrapped and the dimensions of the wrapping material, the control device carries out one or more actions selected from the group consisting of:
- moving at least the folding device or the first and second folding device such with respect to the wrapping material that the wrapping material is engaged at points depending on the measured dimensions of the products to be wrapped and the dimensions of the wrapping material,
- moving the folding fingers of the second arm over a distance to between the folding fingers of the first arm, which distance depends on the measured dimensions of the products to be wrapped and the dimensions of the wrapping material,
- moving the folding pin and the retaining strip depending on the measured dimensions of the products to be wrapped and the dimensions of the wrapping material. In that way it is possible to correctly wrap products in wrapping material in an automated manner.

In an embodiment the folding assembly is furthermore provided with a labelling device for by means of a label closing the folded wrapping material. In this way the folded wrapping material can be reproducibly and reliably closed, and it is also possible to place an indication on the label, for instance relating to the contents of the package, the purpose of the package, the packaging date and the like.

In an embodiment the folding assembly is further provided with a supply roll for wrapping material, which supply roll is suitable for containing surgical sheet as wrapping material. Although the invention is suitable to make use of various types of wrapping material, the invention can be used highly advantageously in the wrapping of medical instruments in surgical sheets, also called BTC ("back table cover").

In an embodiment the folding assembly is further provided with product carriers, wherein each product carrier is adapted for carrying the one or more products to be wrapped. In an embodiment the product carrier is provided with a bottom, with two side walls, wherein the height of the side walls is adjustable, and with a rear wall that can be moved across the bottom, wherein opposite the rear wall the product carrier is open. In that way the height of the side walls can be adjusted to the height of the products to be wrapped, and it is easily possible to move the products to be wrapped out of the product carrier onto the wrapping material via the open rear wall.

According to a third aspect the invention provides a method for making a fold in a first direction in a foldable wrapping material or in material to be wrapped, wherein the method comprises the following steps:

providing a folding device as described above;
moving the folding device such with respect to the wrapping material or the material to be wrapped, that the wrapping material or the material to be wrapped is engaged at least near an edge in the first direction;
moving the folding fingers of the second arm over a distance to between the folding fingers of the first arm for passing the wrapping material or material to be wrapped between the folding fingers for making the fold.

The aspects and measures described in this description and the claims of the application and/or shown in the drawings of this application may where possible also be used individually. Said individual aspects may be the subject of divisional patent applications relating thereto. This particularly applies to the measures and aspects that are described per se in the sub claims.

SHORT DESCRIPTION OF THE DRAWINGS

The invention will be elucidated on the basis of a number of exemplary embodiments shown in the attached drawings, in which.

DETAILED DESCRIPTION OF THE DRAWINGS

The invention will be described below on the basis of wrapping medical instruments or medical equipment in a surgical sheet. However, it will be clear that the invention also relates to wrapping other products and it will also be clear that other wrapping material can be used.

Figures 1A, 1B, 1C, 1D:
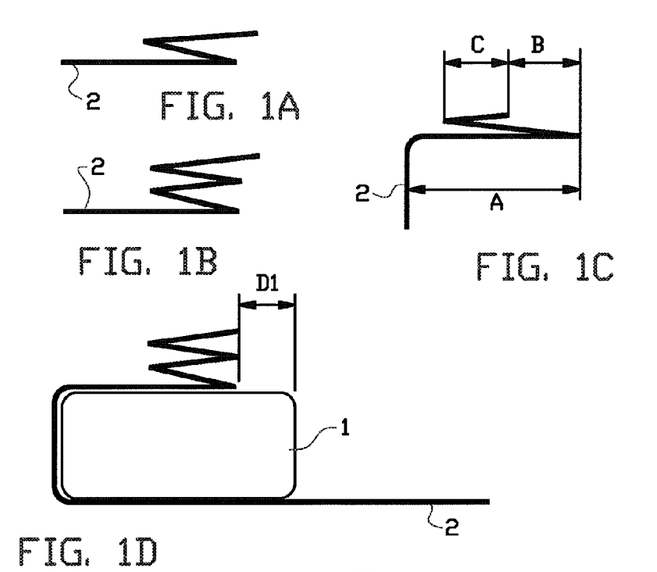
FIGS. 1A-1F schematically show a 2-fold and a 4-fold, as well as the dimensions that are of importance in wrapping medical instruments in surgical sheets.
Figure 1E:
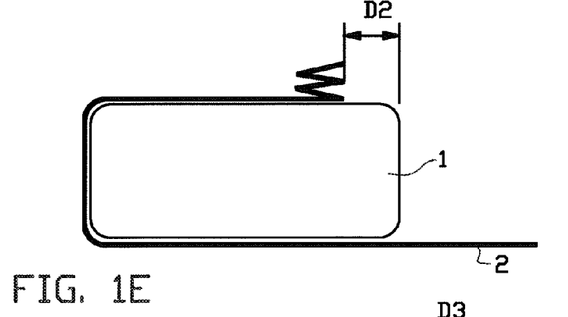
Figure 1F:
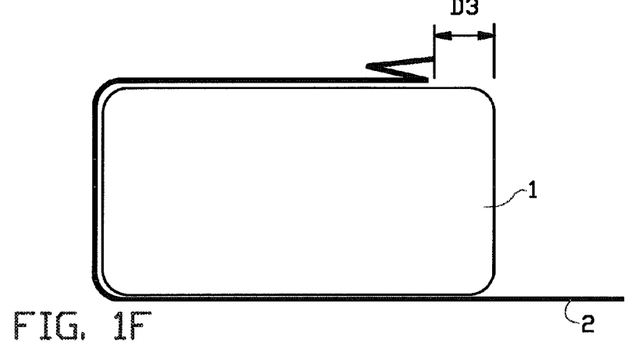

In FIGS. 1A-1F a 2-fold and a 4-fold are schematically shown, as well as the dimensions that are of importance in wrapping medical instruments or equipment (generally indicated with reference number 1) in surgical sheets 2 (in FIGS. 1A-1C only a part of a surgical sheet is shown). Said folds and dimensions are also used when wrapping takes place manually, and they are determined such that the wrapping or packaging takes place sterilely, and also while observing the wishes of the final user, in this case for instance the surgeon.

The dimensions of the surgical sheet 2 are determined by the operating table or an instrument table in an operating room or theatre, and namely such that the operating table or instrument table is at least almost fully covered once the surgical sheet 2 is unfolded. As the dimensions of the medical instruments and equipment 1 to be wrapped may differ, among others depending on the medical procedure to be performed, it proved necessary that for obtaining a correct packaging a longitudinal fold either in the form of a 2-fold (FIG. 1A: for relatively larger medical products to be wrapped) or in the form of a 4-fold (FIG. 1B: for relatively smaller or average-sized medical products) has to be made. Furthermore for wrapping the medical products 1 sterilely in the surgical sheet 2 the dimensions A,B,C,D1 (for a small packaging having a relative wide 4-fold), D2 (for a packaging of average dimensions and a narrow 4-fold) and D3 (for a large packaging having a narrow 2-fold) as shown in FIGS. 1C-1F are of importance. Said dimensions had already been used in the known manual wrapping of the medical products. As will be explained below, the device according to the invention is without a doubt capable of using said dimensions accurately and reproducibly in the wrapping of medical products in surgical sheets.

Figure 2:
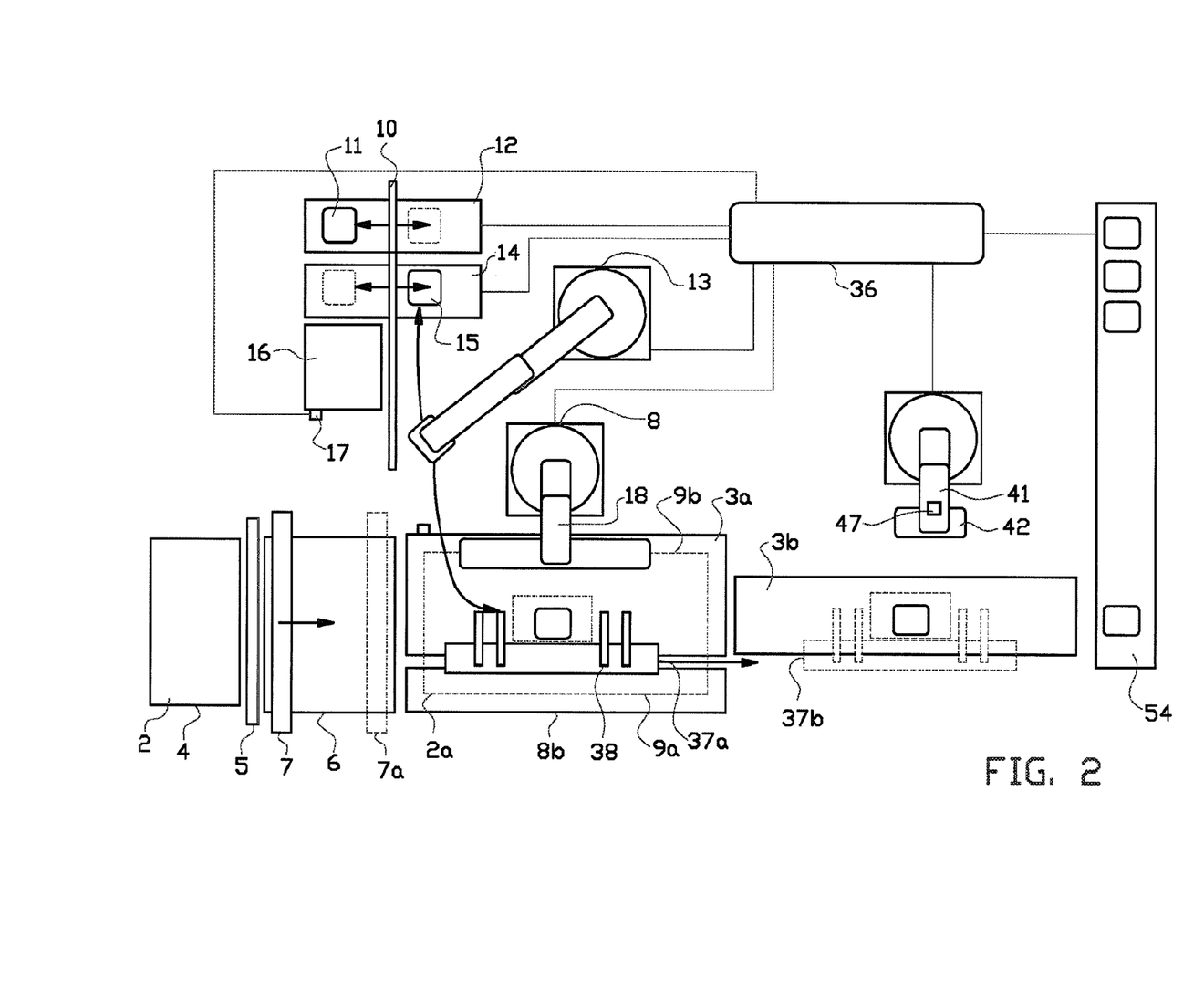
FIG. 2 schematically shows a top view of an assembly for in a rectangular surgical sheet wrapping one or more medical instruments to be wrapped.

FIG. 2 schematically shows a top view of an exemplary embodiment of an assembly for wrapping one or more medical instruments to be wrapped in a rectangular surgical sheet 2a. The assembly comprises a table on which the surgical sheet 2a is placed. In the embodiment shown the table comprises a longitudinal folding section 3a, where longitudinal folds are made in the surgical sheet, and a transverse folding section 3b, where transverse folds are made in the surgical sheet.

In the exemplary embodiment shown in FIG. 2 the assembly comprises a supply roll 4 for wrapping material, which supply roll 4 is suitable for containing surgical sheet 2 as wrapping material. In order to customise the dimensions of the sheet present on the supply roll 4, the device comprises a cutting device 5 and a cutting table 6. A reciprocally movable gripping device 7 is provided for engaging an end of the sheet wound on the supply roll 4 and is suitable for in the direction indicated by the arrow pulling the sheet over the cutting table 6 to a position 7a indicated by broken lines. Subsequently the cutting device 5 is activated in order to give the surgical sheet 2 the desired rectangular dimensions. Such cutting devices and gripping devices are known per se and need not be elaborately described here.

The device furthermore comprises a wrapping material placement device 8 for placing the rectangular surgical sheet 2a on the table 3a, wherein a rectangular wrapping material comprises a first longitudinal side 9a and a second longitudinal side 9b situated opposite thereto. The wrapping material placement means 8 in the embodiment shown comprises a robot arm 18 rotatable over several axles and having wrapping material grippers (mechanical grippers or for instance means for gripping by means of vacuum) for the surgical sheet 2.

In the embodiment shown in FIG. 2 the assembly comprises empty product carriers 11 (further elucidated below), wherein each product carrier 11 is adapted for carrying the one or more products to be wrapped. The empty product carrier 11 is placed on a loading position of a conveyor 12, 14. After loading the product carrier 11 is moved by the conveyor 12 to a pick-up position for the product placement device 13. In the same way the product carrier 15 is transported by the conveyor 14 from a loading position to the pick-up position. Between the loading position and the pick-up position a safety screen 10 is placed, wherein the product carriers 11, 15 are transported through an opening thereof. The loading position is situated at a side of the safety screen 10 that faces away from the product placement device 13, whereas the pick-up position is situated at a side of the safety screen 10 that faces the product placement device 13.

The product placement device 13, in the exemplary embodiment shown a robot arm rotatable about several axles and having a gripper for the product carriers, picks the full product carrier 11, 15 up from the conveyor 12, 14 and takes the full product carrier 11, 15 to the longitudinal folding table 3a. The product carrier 11, 15 is unloaded on the longitudinal folding table 3a, wherein the medical products are placed on the surgical sheet 2a. Subsequently the empty product carrier 11, 15 is placed back in the same position on the conveyor 12, 14 by the product placement device 13.

Near the loading position of the conveyors 11, 14 a measurement table 16 is placed. On the measurement table 16 the dimensions (height, width and depth and optionally volume) of the objects to be wrapped are determined by means of a measurement device 17. As measurement device 17 all devices known for that purpose can be used for measuring the dimensions of the products to be wrapped, such as for instance three or more cameras with image recognition equipment connected thereto. The measurement device 17 is also suitable for generating and giving signals that are indicative of the measured dimensions. The measurement results of the measurement device 17 can be delivered as parameters to a control device 36 of the assembly.

In a simple alternative embodiment the dimensions of the objects to be wrapped are manually determined on the measurement table 16 and via an input means 17 the measurement results are entered as parameters for the control device 36.

Usually the dimensions are determined once per batch, and the resulting parameters are used during the wrapping of all products belonging to the batch in question.

In some cases the products to be wrapped can be pressed in, and in that case the measurement device 17 carries out at least two measurements of the dimensions, wherein one measurement is carried out after a pressure plate has been placed on the products to be wrapped, which plate with relatively little pressure has pushed the products to be wrapped in the direction towards the product carrier.

When the products have been placed on the surgical sheet 2a, a longitudinal fold is made in the rectangular surgical sheet 2a by means of a longitudinal folding device, in the embodiment shown comprising a robot arm 18 rotatable over several axles and bearing longitudinal folding means to be clarified below. Although in the embodiment shown in FIG. 2 the wrapping material placement device 8 and the longitudinal folding device are borne by the same robot arm 18, it is of course possible in an alternative embodiment to use several robot arms.

Figure 3:
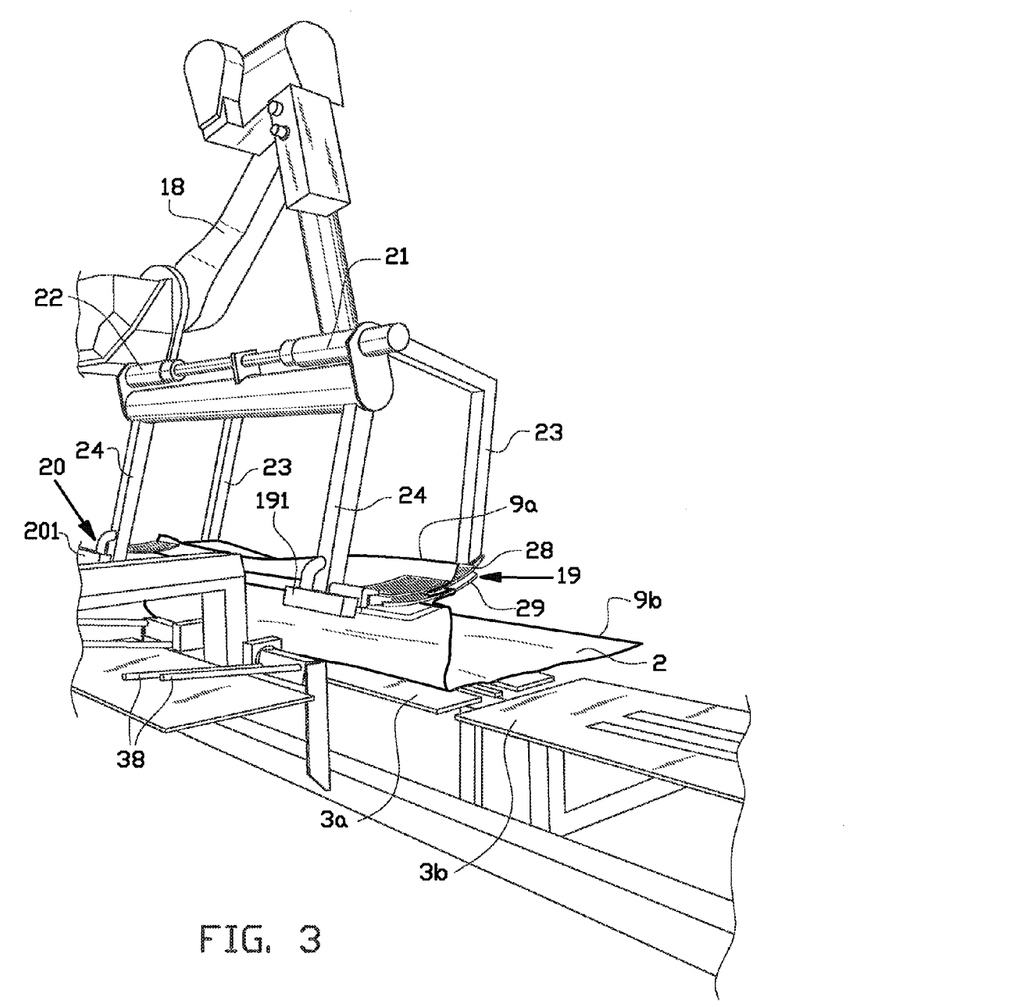
FIG. 3 schematically shows in perspective a first exemplary embodiment of a longitudinal folding device of an assembly according to the invention.
Figure 4:
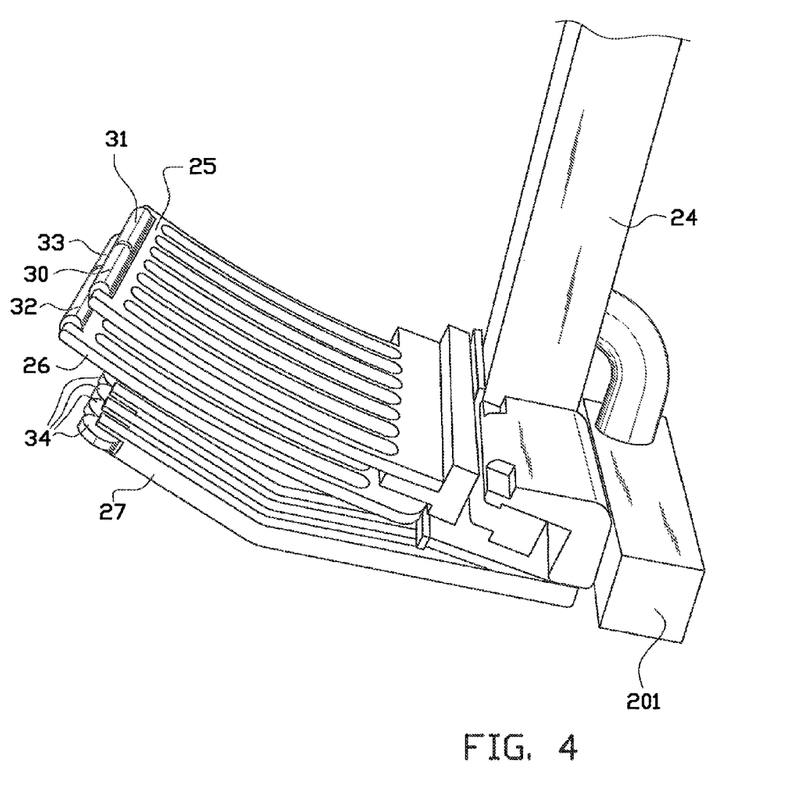
FIG. 4 schematically shows in perspective the folding fingers and clamping fingers of a first folding device of the longitudinal folding device of FIG. 3.

On the basis of FIG. 3, in which schematically in perspective an example of a longitudinal folding device according to the invention is shown, and on the basis of FIG. 4, in which schematically in perspective the folding fingers of a first folding device are shown, the longitudinal folding unit and the wrapping material grippers will be further elucidated.

The longitudinal folding device in this exemplary embodiment comprises two folding devices 19, 20 that can be moved apart and towards each other by means of for instance the cylinders 21, 22. One of the folding devices 19 engages the surgical sheet 2 at least near an outer end of the first longitudinal side 9 thereof and the other folding device 20 engages the surgical sheet 2 at least near the other outer end of the first longitudinal side 9.

In that case each folding device 19, 20 has a first and a second arm 24 and 23, respectively, that can be moved apart and towards each other. The first arm 24 considered in the direction of the first arm 24, has two longitudinal folding fingers 25, 26 that are spaced apart from each other, and considered in the direction of the first arm 24 a clamping finger 35b (see FIG. 5A) spaced apart from the longitudinal folding fingers 25, 26. The second arm 23, considered in the direction of the second arm 23, comprises two longitudinal folding fingers 28, 29 spaced apart from each other, and considered in the direction of the second arm 23 a clamping finger 35a (see FIG. 5A) spaced apart from the longitudinal folding fingers 28, 29. The longitudinal folding fingers 25-29 of an arm 23, 24 extend substantially transverse to the arm 23, 24, wherein the longitudinal folding fingers 28, 29 of the second arm 23 are movable to between the outer longitudinal folding finger 25 and the clamping finger 35b, and on both sides of the middle longitudinal folding finger 26 of the first arm 24. The clamping finger 35a of the second arm is movable to against the clamping finger 35b of the first arm 24 for clamping the wrapping material 2 to be folded between them.

In FIG. 4 it is clearly visible that each longitudinal folding finger 25,26 is planar (or grid-shaped), wherein the free outer end of each longitudinal folding finger 25,26 extends substantially transverse to the arm 24, and during making a fold extends substantially parallel to the fold. The free outer ends of each longitudinal folding finger 25 and 26 are also provided with at least one roller 30-34, wherein the axis of rotation of the rollers 30-33 extends substantially parallel to the free outer ends, in order to facilitate folding. The free outer end of the clamping finger 35b is also provided with rollers 34. However, the axis of rotation of the rollers 34 is substantially transverse to the axis of rotation of the rollers 30-33 of the folding fingers 25, 26 in order to ensure clamping, at least during folding. The rollers 34 of the clamping finger 35b are able to roll in longitudinal direction.

It will be clear that the robot arm 18 according to this exemplary embodiment is adapted for moving the longitudinal folding device such that the folding devices 19, 20 are movable to in a position on both sides of the first 9a and second 9b longitudinal side of the surgical sheet 2a placed on the table.

The robot arm 18 is also movable to place the wrapping material 2 on the table 3a. For that purpose the folding devices 19, 20 according to this exemplary embodiment are provided with wrapping material grippers 191, 201 as shown in FIGS. 3 and 4.

In FIGS. 5A-5D making a 2-fold and a 4-fold, respectively, in a surgical sheet 2 by means of the longitudinal folding fingers 25-29 of a folding unit 19, is schematically shown.

Figure 5A:
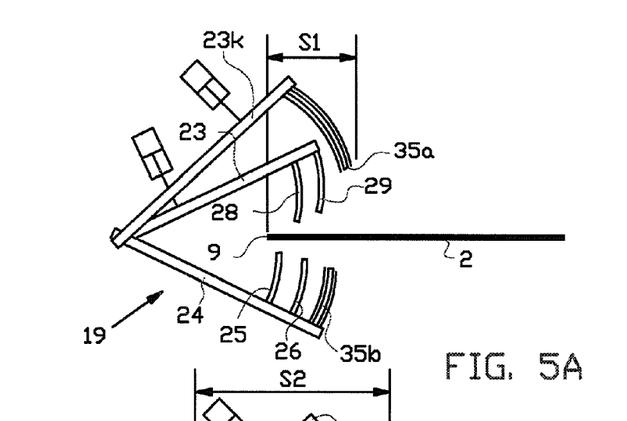
FIGS. 5A-5D schematically show making a 2-fold and a 4-fold, respectively, in a surgical sheet by means of the longitudinal folding fingers of the folding device of FIG. 4.
Figure 5B:
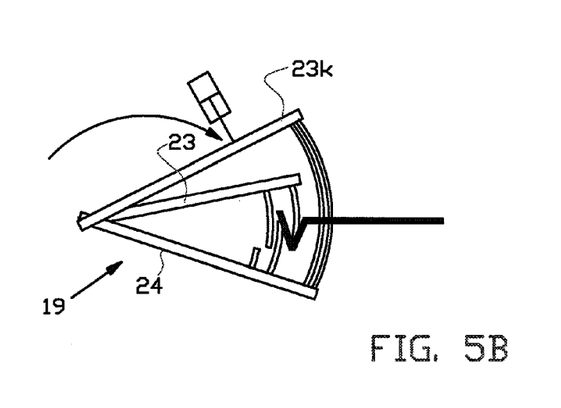

In FIGS. 5A and 5B the making of a 2-fold is shown. Here the folding unit 19 is placed such with respect to the surgical sheet 2 that the longitudinal side 9 of the surgical sheet 2 extends over a relatively short distance s1 between both arms 23, 24 (FIG. 5A). Subsequently the clamping arm 23k is activated, wherein the surgical sheet 2 is clamped between the outer ends of the clamping fingers 35a, 35b. After that the arms 23, 24 are moved towards each other over a certain distance, wherein the distance over which the longitudinal folding fingers 25-29 interlock (in other words overlap each other) defines the width of the 2-fold.

Figure 5C:
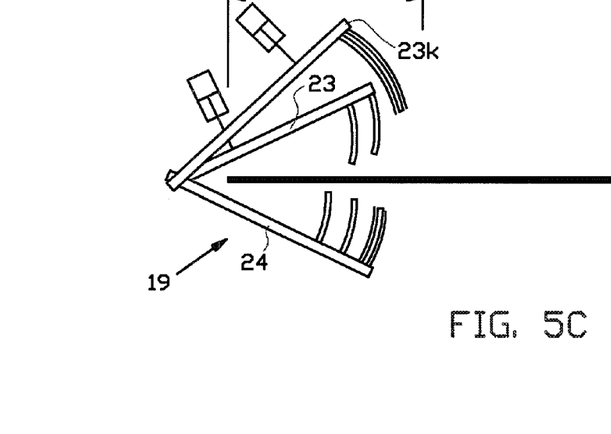
Figure 5D:
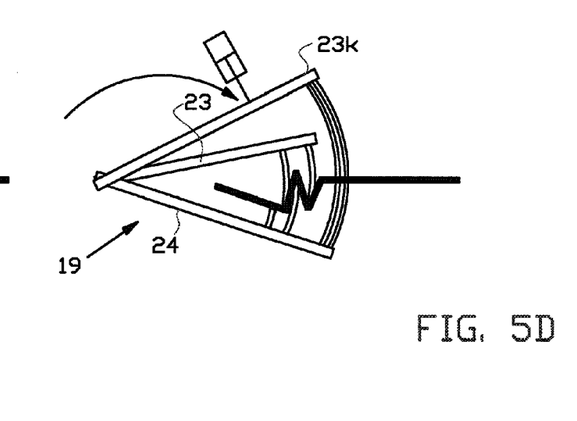
Figure 6A:
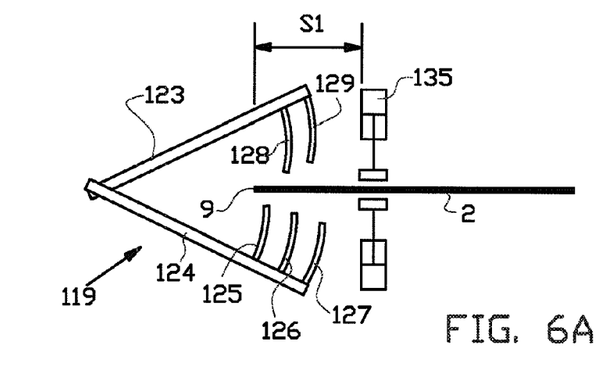
FIGS. 6A-6D schematically show making a 2-fold and a 4-fold, respectively, in a surgical sheet by means of the longitudinal folding fingers of a second exemplary embodiment of a folding unit and a clamping unit.
Figure 6B:
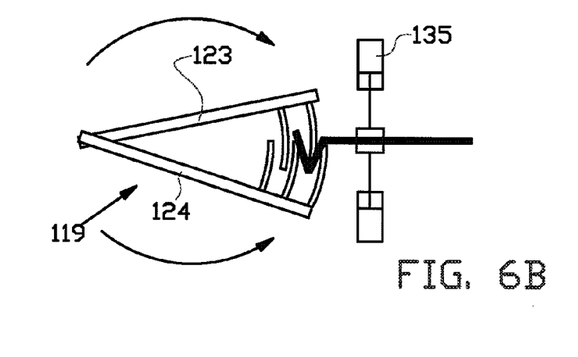
Figure 6C:
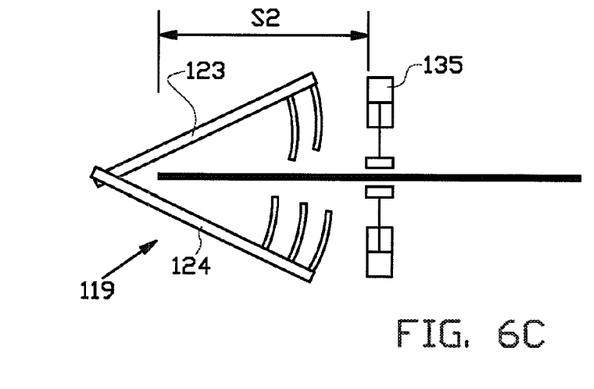
Figure 6D:
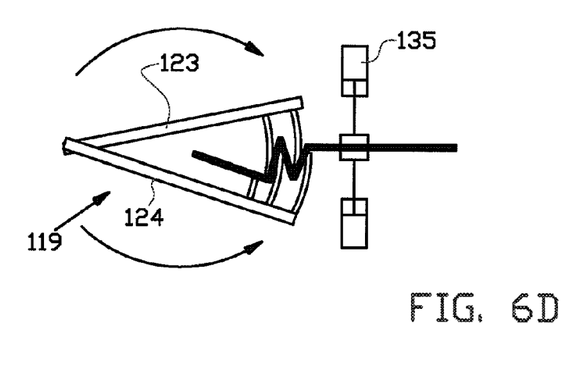

In FIGS. 5C and 5D the situation is shown in which the folding unit 19 is placed such with respect to the surgical sheet 2 that the longitudinal side 9 of the surgical sheet 2 extends over a relatively large distance s2 between both arms 23, 24 (FIG. 5C). Subsequently the clamping arm 23k is activated, wherein the surgical sheet 2 is clamped between the outer ends of the clamping fingers 35a, 35b. After that the arms 23, 24 are moved towards each other over a certain distance, wherein the distance over which the longitudinal folding fingers 25-29 interlock (in other words overlap each other) defines the width of the 4-fold.

In both cases the rollers on the outer ends of the fingers ensure that the surgical sheet is able to move between the fingers. Prior to the longitudinal fingers moving towards each other, the surgical sheet 2 is clamped fixed by a clamping mechanism 35a, 35b. As an alternative of this mechanic clamping mechanism, optionally a clamping mechanism that operates by means of generating vacuum can also be used.

In the embodiment as shown in the FIGS. 5A-5D a first part 35b of the clamping mechanism is placed on the first arm 24. A pneumatically or hydraulically driven second arm 23 with folding fingers 28, 29 and a pneumatically or hydraulically driven clamping arm 23k that can be driven independent from the second arm 23, are further provided. Thus this exemplary embodiment provides a combined folding and clamping device, wherein the first arm 24 can be fixedly connected to the outer end of the robot arm 18.

In FIGS. 6A-6D the making of a 2-fold or 4-fold, respectively, in a surgical sheet 2 by means of the longitudinal folding fingers 125-129 of a folding unit 119 is schematically shown, in a manner comparable to what has been shown in FIGS. 5A-5D and as described above. However, this embodiment is provided with separate clamping units 135.

Both embodiments of FIGS. 5A-5D and 6A-6D have in common that the surgical sheet 2 is clamped at a certain distance s1, s2 to the longitudinal side 9 and that the part of the surgical sheet 2 is folded between the clamped position and the longitudinal side in a zigzag form. The distance s1, s2 among others depends on the dimensions of the material to be wrapped and the dimensions of the surgical sheet 2. In an embodiment the surgical sheet 2 is clamped at such a distance from the material to be wrapped, that the surplus of surgical sheet 2 that is folded in the zigzag form, can be placed on top of the material to be wrapped as described in more detail below.

Figure 7A:
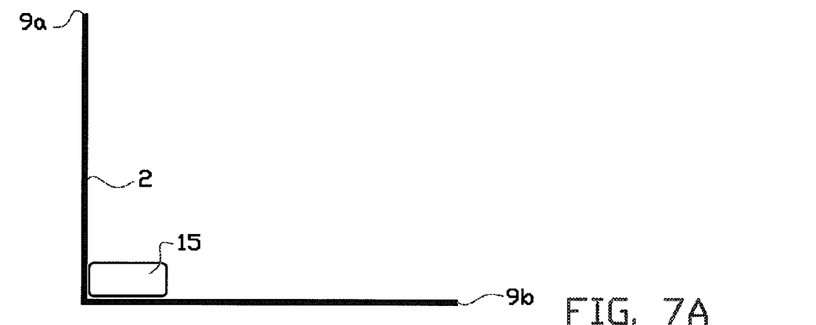
FIGS. 7A-7F show some steps of wrapping medical instruments to be wrapped in a surgical sheet using an assembly according to the invention.
Figure 7B:
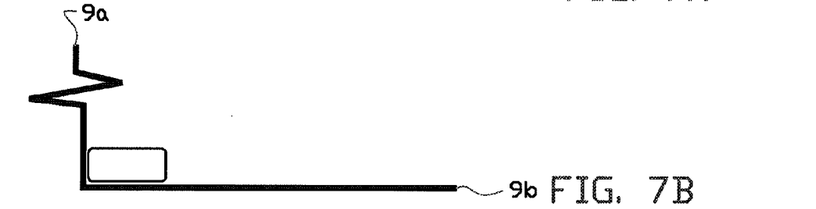
Figure 7C:
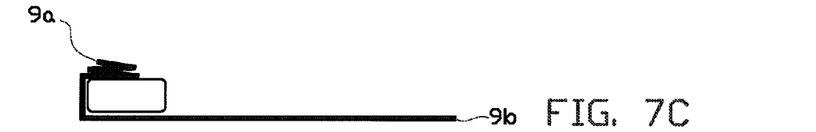
Figure 7D:
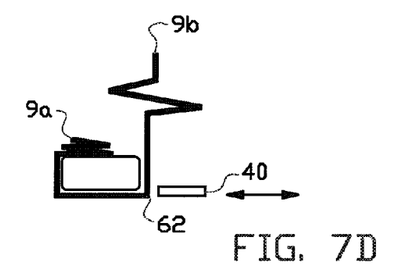
Figure 7E:
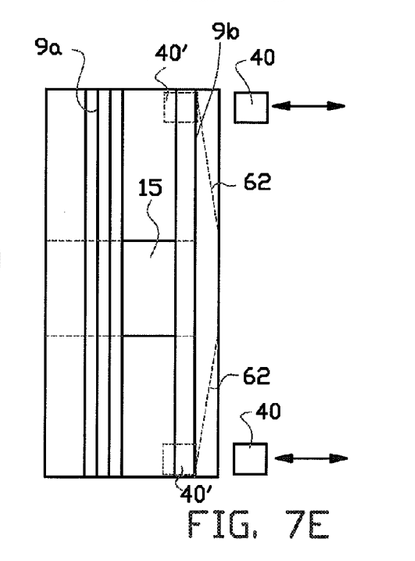
Figure 7F:
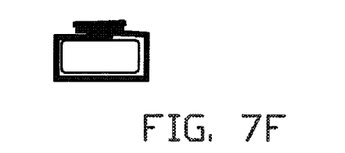

In FIGS. 7A-7F a few steps in the wrapping of medical instruments to be wrapped in a surgical sheet 2 are further schematically elucidated, wherein FIG. 7E is a top view of FIG. 7D. The longitudinal fold in the surgical sheet 2 near the longitudinal side 9a is made after the longitudinal folding device, during engaging the surgical sheet, has moved the longitudinal side 9a to at a distance above the table, as shown in FIG. 7A. In that way the surgical sheet 2 is placed partially vertically. To that end the folding devices 19, 20 can be moved to a distance above the table 3a. After the longitudinal fold has been made by having the longitudinal folding fingers interlock (FIG. 7B) the longitudinal folding device is moved such that the longitudinal fold is placed on the products 15 to be wrapped (FIG. 7C).

Now a transfer unit 37 comprising two sets of two transfer pins 38 (FIGS. 2 and 7) is moved to the longitudinal folding table 3a (in FIG. 2 shown by full lines and reference number 37a). In that case the transfer pins 38 are moved in the direction of the table 3a (for instance by folding them down on the table), so that the surgical sheet 2 is somewhat tautened. Particularly during this tautening it may be advantageous when the clamping fingers are provided with the rollers 34 as shown in FIG. 4. As a result the surgical sheet 2 is able to move between the rollers 34 in longitudinal direction during tautening and simultaneously clamping can be ensured in the direction substantially perpendicular to the longitudinal direction.

Moreover in that case a retaining strip 39 (FIG. 8) is placed on the part of the surgical sheet above the products to be wrapped, and the retaining strip 39 is moved in a direction transverse to the table 3a. For that purpose the retaining strip 39 is movable for making a vertical stroke in the direction of the table 3a in order to keep the surgical sheet 2 slightly pressingly in the correct position. It is noted here that the retaining strip 39 in the embodiment shown is moved from a position adjacent to the table 3a to a position above the products to be wrapped according to a plane that is at least almost parallel to the table 3a, that the retaining strip 39 preferably is also adapted for making a horizontal stroke in the longitudinal direction for positioning the strip 39 with respect to the material to be wrapped, and that the movement of the retaining strip 39 for obtaining the pressing is slight.

The retaining pins 38 on the other hand can be swung from an inactive position (see FIG. 3) to an active position (as shown in FIG. 2) by means of a rotation or swinging motion of at least approximately 90°, preferably approximately 180°.

After that or simultaneously therewith the folding devices are moved from a position on both sides of the first longitudinal side 9a of the surgical sheet 2 placed on the table 3a to a position on both sides of the second longitudinal side 9b of the surgical sheet 2 placed on the table 3a, for making the second longitudinal fold at that location (see FIG. 7D). Said second longitudinal fold is made in the same manner as the first longitudinal fold. Prior to the longitudinal folding units placing the longitudinal side 9b with the second longitudinal fold on top of the products to be wrapped (FIG. 7E), the transfer pins 38 are swung back into the inactive position. The longitudinal side 10 is placed above the products to be wrapped, after which the retaining strip 39 is retracted. After that both the transfer pins 38 and the retaining strip are placed on top of the second longitudinal fold. Optionally the device may comprise two pressure strips 40 which after the second longitudinal side 10 has been placed vertically, can be moved into a position 40' as shown by broken lines in FIG. 7E, so that a folding edge 62 of the surgical sheet at the free ends thereof narrows down, as indicated by the broken lines in FIG. 7E. Said narrowing facilitates the later correct arrangement of the transverse folds.

Figure 8:
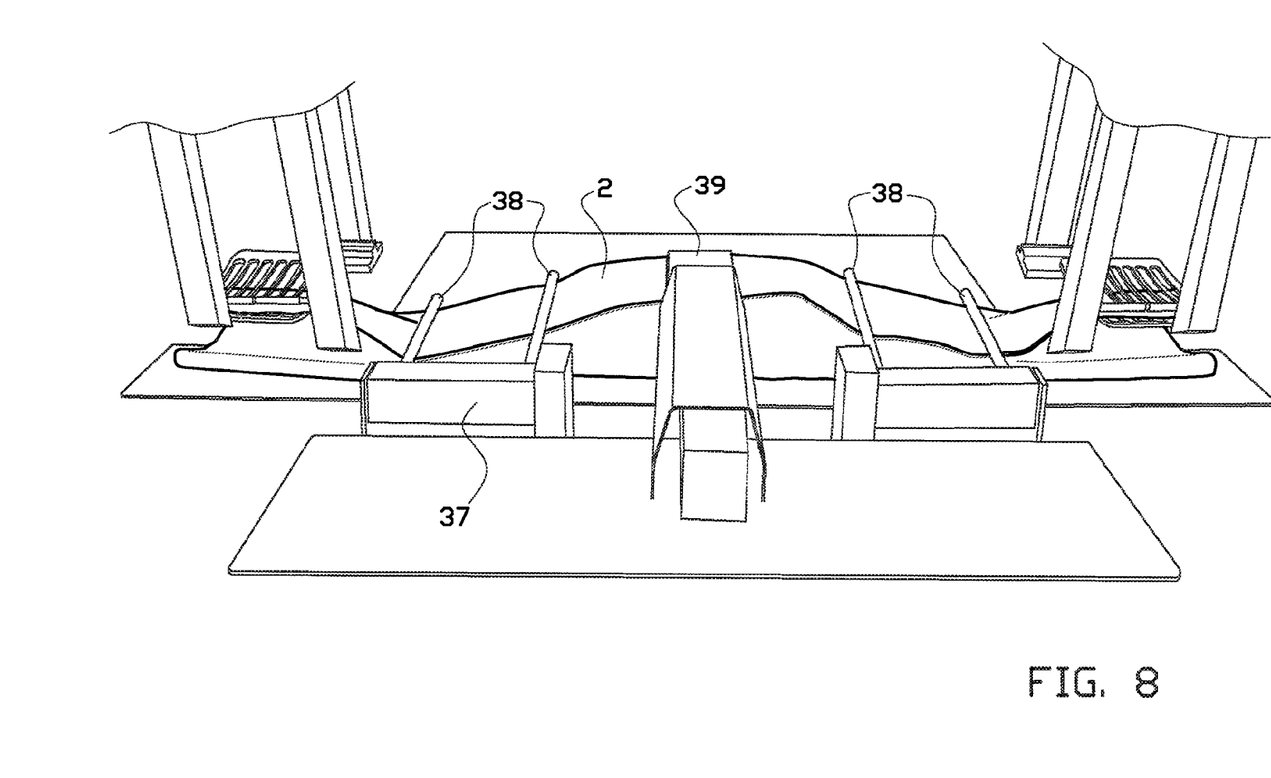
FIG. 8 schematically shows a transfer unit with transfer pins for transferring the surgical sheet from a longitudinal folding table to a transverse folding table to be used in an assembly according to the invention.

The transfer unit 37, as shown in FIG. 8, can be moved between the longitudinal folding table 3a and the transverse folding table 3b over a rail (not shown). A robot arm 41 rotatable over several axles and provided with a gripper 42 for engaging a transverse edge of the surgical sheet engages the transverse side of the surgical sheet which side is oriented to the transverse folding table 3b, and pulls the surgical sheet 2 from the longitudinal folding table 3a to the transverse folding table 3b (see FIG. 2). Simultaneously the transfer unit 37 moves from the position shown with reference number 37a to the position as shown with the reference number 37b. Thus the surgical sheet with the products to be wrapped is transferred from the table 3a to the transverse folding table 3b.

Figures 9A, 9B:
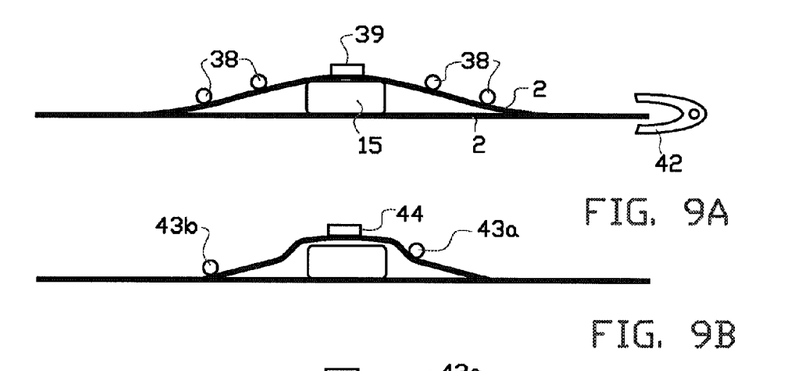
FIGS. 9A-9G schematically show some steps of by means of a transverse folding device folding a transverse fold in a surgical sheet.

For making transverse folds in the surgical sheet positioned on the transverse folding table 3b, the device comprises a transverse folding means, that is schematically shown in FIGS. 9A-9G. The transverse folding means is provided with a number of transverse folding pins 43a, 43b, and also comprises a retaining strip 44. After the transfer unit 37 has arrived in the position 37b (FIG. 9A), the folding pins 43a, 43b are extended from an inoperative position over the package to be folded and the retaining strip 44 is placed on top of the retaining strip 39. After that the transfer pins 38 and the retaining strip 39 are retracted and the transfer unit 37 moves back to the longitudinal folding table 3a. The folding pins 43a, 43b and the retaining strip 44 take over the function of retaining the surgical sheet 2 from the corresponding elements of the transfer unit (FIG. 9B).

The folding pins 43a, 43b therefore are movable from an inoperative position to a position extending transverse to the longitudinal sides of the wrapping material. In an embodiment the folding pins may for instance be placed on the surgical sheet by rotating or folding down, however preferably the folding pins are extendable from an inactive position and retractable to the inactive position. In addition the two folding pins 43a, 43b are each movable within a certain range as regards length and height with respect to the table 3a.

In an embodiment at least one folding pin 43a, 43b is provided with an inclined front side, as a result of which folding to the inside is facilitated. In that case the inclined front side is oriented towards the fold.

Figures 9C, 9D:
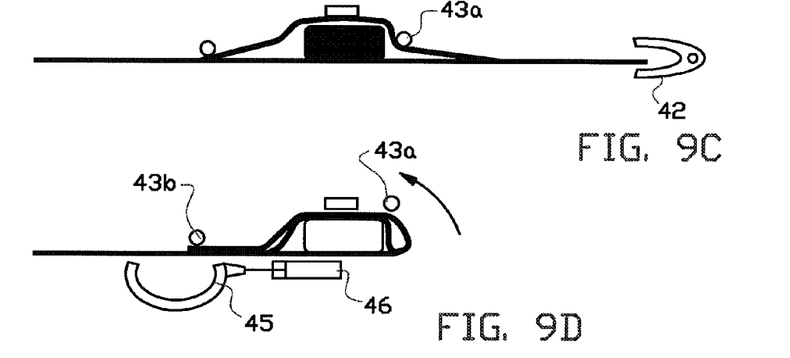
Figure 9E:
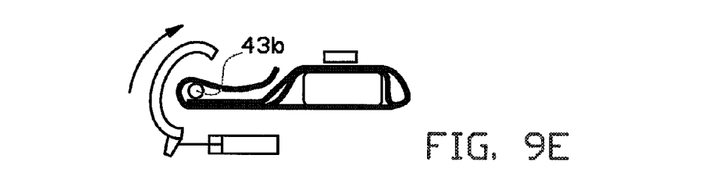
Figure 9F:
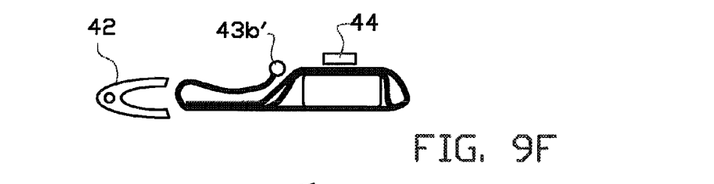

For the purpose of making the first transverse fold the folding pin 43a is first moved a little to the table 3b and the gripper 42 engages a transverse edge of the surgical sheet 2 (FIG. 9C). Due to movement of the robot arm 41 the gripper is now moved such to over and past the folding pin 43a that the first transverse fold is made. In the last stage of this folding motion the folding pin 43a and the retaining strip 44 are retracted and subsequently placed again on top of the part of the surgical sheet that has been folded back (FIG. 9D) and pressed slightly downwards. The gripper 42 pulls the transverse edge of the surgical sheet a little further in order to tauten the surgical sheet, that means at a pre-defined tension, after which the retaining strip and the folding pin 43a are moved a little further downwards in order to retain the folded surgical sheet. In addition to the gripper 42 a folding mechanism 45 is provided for folding the surgical sheet (FIG. 9E) back over the folding pin 43b. The folding mechanism 45 as shown is designed as cup-shaped hand rotatable by a cylinder 46. It is noted that in the embodiment shown the folding pin 43a is placed close to the products to be wrapped, whereas the folding pin 43b is placed at some distance therefrom.

Figure 9G:
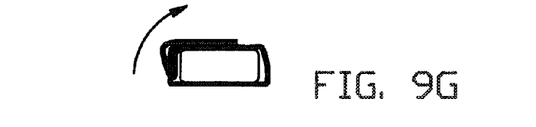

Subsequently the surgical sheet is engaged by the gripper 42 at the part that has just been folded back over the folding pin 43b (FIG. 9F), wherein just before engaging the folding pin 43b is retracted. The folding pin 43b is then placed in a position shown with reference number 43b' closer to the products to be wrapped, and pressed slightly towards the table 3b, after which the gripper makes the third transverse fold in the surgical sheet. In the last part of this motion the folding pin 43b' and the retaining strip 44 are retracted. Thus the packaging as shown in FIG. 9G is obtained. It is noted that contrary to the transfer pins of the transfer unit, the folding pins besides the fact that they are rotatable or can be folded down they can also be moved in a direction in the plane of the table into a position adjacent to the table. In order to close the package obtained the robot arm 41 adjacent to the gripper 42 comprises a labelling device 47 (FIG. 2) for by means of a label closing the folded surgical sheet. Subsequently the closed packages are discharged via a discharge conveyor 54 (FIG. 2).

The operation of the device in an embodiment is controlled by a control device 36 (FIG. 2). Said control device 36 controls the operation of the parts in question at least also on the basis of the measurement signals resulting from the manual measurements or the measurement device 17, that are indicative of the dimensions of the medical products to be wrapped. For that purpose the control device 36 (wired or wireless) is connected to the measurement device 17 or an input device, for instance a keyboard, near the measurement table 16. The control device 36 controls at least the operation of the longitudinal folding means, the transverse folding means and the transfer unit (among others its pins and its retaining strips). On the basis of the measured dimensions of the medical products to be wrapped and the dimensions of the surgical sheet, the control device 36 controls the individual parts such that:

the longitudinal folding units are moved such with respect to the surgical sheet that the surgical sheet is engaged at points depending on the measured overall dimension of the products to be wrapped and the dimensions of the wrapping material, moving the longitudinal folding fingers of the second arm over a distance to between the outer longitudinal folding fingers and on both sides of the middle longitudinal folding finger of the first arm, which distance depends on the measured overall dimension of the products to be wrapped and the dimensions of the wrapping material, moving the pins and the retaining strips depending on the measured overall dimension of the products to be wrapped and the dimensions of the wrapping material. All this such that the desired sizes A,B,C, and D as shown in FIG. 1 can be obtained.

Figure 10:
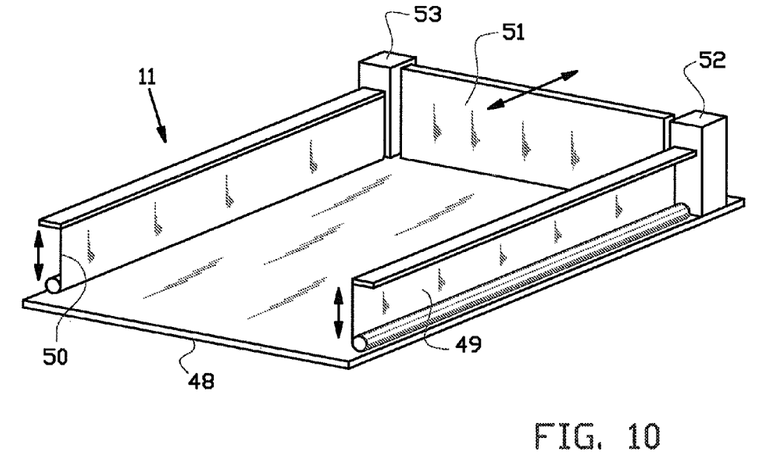
FIG. 10 shows a schematic side view of a product carrier for carrying medical instruments to be wrapped.

The product carriers 11 used in the device are provided with a bottom 48, with two side walls 49, 50, wherein the height of the side walls 49, 50 can be adjusted and with a rear wall 51 that can be moved over the bottom 48, wherein the product carrier 11 is open opposite the rear wall 51, as shown in FIG. 10. The side walls 49, 50 may have the form of roller blinds that can be moved up or down along the supports 52, 53. The height of the side walls is adjustable to the measured height of the medical products to be wrapped. The rear wall 51 can for instance be shifted through a cylinder device arranged on the product placement means. Due to the relative shifting of the rear wall with respect to the bottom, the products present on the bottom are shifted off from the bottom. This takes place such in the embodiment shown in the figures that when the product placement means has placed the full product carrier on the surgical sheet the cylinder is activated, and simultaneously the product placement means itself is moved in opposite direction, so that the rear wall with respect to the surgical sheet assumes a fixed position and the bottom and the side walls of the surgical sheet are moved away so that the products present on the bottom are shifted onto the surgical sheet.

The above description is included to illustrate the operation of preferred embodiments of the invention and not to limit the scope of the invention. Starting from the above explanation many variations that fall within the spirit and scope of the present invention will be evident to an expert, particularly as defined in the attached claims.

The invention claimed is:

1. Folding assembly for wrapping one or more products to be wrapped in a wrapping material, which assembly is provided with:
   a table,
   a wrapping material placement means for placing the wrapping material on the table, wherein the wrapping material comprises a first longitudinal side and a second longitudinal side situated opposite thereto, a product placement means for placing the one or more products to be wrapped on the wrapping material placed on the table, a folding device for making a fold in a first direction in the wrapping material, wherein the folding device comprises a clamping unit and a folding unit, the clamping unit comprising first and second clamping fingers, which with respect to each other can be moved apart and towards each other for clamping the wrapping material in between them at a clamped position at a certain distance to the first longitudinal side, the folding unit being placed next to the clamping unit in a direction substantially transverse to the first direction between the clamped position and the first longitudinal side, and comprising a first and a second folding arm, which with respect to each other can be moved apart and towards each other, the first folding arm comprising two first folding fingers that extend in a direction of the first folding arm and are spaced apart from each other substantially transverse to the first direction, the second folding arm comprising at least one second folding finger that extends in the direction of the first folding arm, the second folding finger of the second arm being movable to between the first folding fingers of the first arm to fold the part of the wrapping material between the clamped position and the first longitudinal side in a zigzag form, wherein the first direction is substantially parallel to the first longitudinal side.

2. Folding assembly according to claim 1, wherein the folding device can be moved up to a distance above the table.

3. Folding assembly according claim 1, wherein the folding device is movable from a position near the first longitudinal side of the wrapping material placed on the table into a position near the second longitudinal side of the wrapping material placed on the table.

4. Folding assembly according to claim 1, furthermore provided with a transverse folding device for making a transverse fold in the wrapping material, which fold runs transverse to the longitudinal sides, wherein the transverse folding device is provided with at least one folding pin that can be moved to a position extending transverse to the longitudinal sides of the wrapping material and with a folding mechanism for folding the wrapping material over the folding pin.

5. Folding assembly according to claim 4, wherein the folding pin is moveable in a direction transverse to the table.

6. Folding assembly according to claim 1, furthermore provided with a retaining strip, that can be moved to above a product placed on the wrapping material, which retaining strip can also be moved in a direction transverse to the table.

7. Folding assembly according to claim 6, which is furthermore provided with a control device for controlling the operation of at least the folding device, the transverse folding device and the retaining strip.

8. Folding assembly according to claim 7, furthermore provided with input means for entering data regarding the dimensions of the products to be wrapped to the control device or furthermore provided with a measurement device for measuring the dimensions of the products to be wrapped and for providing the control device with a signal indicative of the measured dimensions.

9. Folding assembly according to claim 8, wherein based on the dimensions of the products to be wrapped and the dimensions of the wrapping material, the control device carries out one or more actions selected from the group consisting of:

moving at least the first folding device such with respect to the wrapping material that the wrapping material is engaged at points depending on the measured dimensions of the products to be wrapped and the dimensions of the wrapping material, moving the folding fingers of the second arm over a distance to between the folding fingers of the first arm, which distance depends on the measured dimensions of the products to be wrapped and the dimensions of the wrapping material, moving the folding pin and the retaining strip depending on the measured dimensions of the products to be wrapped and the dimensions of the wrapping material.

10. Folding assembly according to claim 1, wherein the folding assembly is provided with a labelling device for by means of a label closing the folded wrapping material.

11. Folding assembly according to claim 1, wherein the folding assembly is provided with a supply roll for wrapping material, which supply roll is suitable for containing surgical sheet as wrapping material.

12. Folding assembly according to claim 1, wherein the folding assembly is provided with product carriers, and wherein each product carrier is adapted for carrying the one or more products to be wrapped.

13. Folding assembly according to claim 12, wherein the product carrier is provided with a bottom, with two side walls, wherein the height of the side walls is adjustable, and with a rear wall that can be moved across the bottom, wherein opposite the rear wall the product carrier is open.

14. Folding assembly according to claim 1, wherein the first clamping finger is movable to against the second clamping finger for clamping the wrapping material to be folded between them.

15. Folding device according to claim 1, wherein the folding fingers each comprise a free outer end and at the free outer ends of each folding finger at least one rotatable folding roller is placed, a rotary shaft of the folding roller being oriented substantially parallel to the first direction.

16. Folding device according to claim 1, wherein the clamping fingers each comprise a free outer end and at the free outer end of at least one of the clamping fingers at least one rotatable clamping roller is placed, a rotary shaft of the clamping roller being oriented substantially transverse to the first direction.

* * * * *